United States Patent [19]

Pierantozzi

[11] Patent Number: 4,851,579
[45] Date of Patent: Jul. 25, 1989

[54] ALKYLATION OF AROMATIC AMINES OVER AL EXCHANGED ZEOLITES

[75] Inventor: Ronald Pierantozzi, Orefield, Pa.

[73] Assignee: Air Products and Chemicals, Inc., Allentown, Pa.

[21] Appl. No.: 35,551

[22] Filed: Apr. 7, 1987

[51] Int. Cl.$^4$ ............................................. C07C 85/24
[52] U.S. Cl. .................................................... 564/409
[58] Field of Search ......................................... 564/409

[56] References Cited

U.S. PATENT DOCUMENTS

| | | | |
|---|---|---|---|
| 2,762,845 | 9/1956 | Stroh et al. | 260/578 |
| 3,178,365 | 4/1965 | Miale | 208/120 |
| 3,201,486 | 8/1965 | Bielawski et al. | 260/671 |
| 3,275,690 | 9/1966 | Stroh et al. | 260/576 |
| 3,281,483 | 11/1966 | Benesl et al. | 260/672 |
| 3,649,693 | 3/1972 | Napolitano | 260/578 |
| 3,923,892 | 12/1975 | Klopfer | 260/578 |
| 4,224,188 | 9/1980 | Alafandi et al. | 252/455 Z |
| 4,259,537 | 3/1981 | Chu | 585/467 |
| 4,393,262 | 7/1983 | Kaeding | 585/467 |
| 4,395,372 | 7/1983 | Kluttz et al. | 260/465 |

FOREIGN PATENT DOCUMENTS

| | | |
|---|---|---|
| 226781 | 7/1987 | European Pat. Off. ............ 564/409 |
| 1051271 | 7/1935 | Fed. Rep. of Germany . |
| 1406739 | 6/1965 | France . |
| 56-110652 | 9/1981 | Japan . |
| 6407636 | 1/1966 | Netherlands . |
| 414574 | 8/1934 | United Kingdom . |

OTHER PUBLICATIONS

Zollner and Marton, Acta Chim. Hung, Tomus 20, 1959 (pp. 321-329), "Some Aspects of the Ethylation of Aniline in the Vapour Phase".

Wang and Lunsford, J. Catalysis, 24, 262-271 (1972), "The Physical Properties and Catalytic Activity of AlHY Zeolites".

B. Wichterlova et al., Proceeding of the Fifth International Zeolite Conference, pp. 373-381, "Aluminum in HY and Satabilized Zeolites".

Primary Examiner—Glennon H. Hollrah
Assistant Examiner—Raymond Covington
Attorney, Agent, or Firm—Keith D. Gourley; James C. Simmons; William F. Marsh

[57] ABSTRACT

This present invention is a process for alkylating aromatic amines to form ortho-alkylated products in high selectivity relative to N-alkylated products. Aromatic amines are contacted with an olefin or an alcohol in the presence of an ion exchanged zeolite in which at least a portion of the exchangeable ion sites have been exchanged with Al cations.

14 Claims, No Drawings

ALKYLATION OF AROMATIC AMINES OVER AL EXCHANGED ZEOLITES

TECHNICAL FIELD

This present invention relates to processesfor the alkylation of aromatic amines in the presence of crystalline molecular sieves. In a preferred embodiment, it relates to processes wherein the product ratio of ortho-alkylated aromatic amines to both para-alkylated and N-alkylated aromatic amines is high.

BACKGROUND OF THE INVENTION

Processes for alkylating a variety of alkylatable aromatic compounds by contacting such compounds with a hydrocarbon radical providing source such as an olefin or alcohol are widely known. Typically, alkylatable aromatic compounds are mononuclear aromatic compouns themselves or those substituted with a hydroxyl, amine or an ether group. The alkylation has been carried out in the prsence of homogeneous and heterogeneous catalyst systems.

Ring alkylated aromatic amines have been some of the products produced by alkylation procedures. Ring alkylated aromatic amines have a variety of used in chemical synthesis. Some of the early uses were intermediates for substituted isocyanates, herbicidal compositions, dyestuffs and textile auxiliary agents. More recently aromatic amines have been utilized as chain lengthening or cross-linking components in polyurethane systems. These are commonly referred to as chaine xtenders.

Representative references which illustrate some of the early processes in forming ring alkylated aromati amines are:

British Pat. No. 414,574 discloses the reaction of aniline with various olefins, e.g., cyclohexene and alcohols,e .g., butanol in the presence of a neutral or weakly acidic catalyst system commonly referred to as hydrosilicates at tempeatures from 200°–270° C. Ortho and paracyclohexylaniline, N-cyclohexylaniline, N0butylaniline and para-methylortho-cyclohexylaniline and N-cyclohexy-para-toluidine are listed as representative products.

AS No. 1,051,271 discloses the ring alkylation of aniline with an olefin, e.g., ethylene, in the presence of akaolin or in the presence of aluminum and aluminum alloys. Alkylation with higher olefins, e.g., propylene, butlene, etc., was carried out in the presence of Friedel-Crafts catalyst or bleaching earths under liquid phase conditions at temperatures from 150°–350° C. Examples of catlytic systems included aluminum chloride, ainz chloride, boron trifluoride, sulfuric acid, phosphoric acid and bleaching earth. Ring alkylation at the ortho-position was predominant, although other products such as the di and tri-alkylated aniline product were produced.

In an article by Zollner and Marton, Acta Chim. Hung. TOmus 20, 1959 (Pages 321–329) the vapor phase alkylation of aniline with ethanol was effected in the presence of aluminum oxide.

U.S. Pat. Nos. 3,649,693 and 3,923,892 discloses the preparation of ring alkylated aromatic amines by reacting an aromatic amine with an olefin in the presence of aluminum anilide, optionally including a Friedel-Crafts promoter. Reaction products include 2-ethylaniline, and 2,6-diethylaniline.

Stroh, et al., in U.S. Pat. Nos. 3,275,690; 2,762,845, Japanese Sho No. 56-110652, and, as mentioned previously, AS No. 1,051,271, disclose various processes for preparing alkylated aromatic amines by reacting an aromatic amine with an olefin in the presence of Friedel-Crafts catalysts as well as a combination of Friedel-Crafts catalysts in teh prsence of halogen compounds combined with aluminum. Representative reaction products included 2-cyclohexylaniline, diethyltoluenediamine, diethylaniline, diisopropylaniline and mono-tert-butylaniline.

The art, e.g., Netherlands Application No. 6,407,636 has recognized that alkylation of various aromatic and heterocyclic compounds can be carried out in the presence of a zeolite having a pore size from 6–15 Angstroms wherein active cationic sites are obtained with an exchangeable metal or hydrogen cations in their ordered internal structure. Alkylating agents include olefins having from 2 to 12 carbon atoms, alkyl halides such as propylbromide and nethylchloride; and alcohols, such as, methanol, ethanol, and propanol. Various compounds were suggested as being suited for alkylation and these include both the heterocyclic and aromatic ring compounds. For aromatic amine alkylatio it was suggested that a zeolite with a sparse distribution of acidic sites should be utilized. It was believed the highly acidic zeolite catalysts which have a high density of acidic sites may bind the amine to the catalyst and block the pore structures. In Example 1 aniline was alkylated with propylene using sodium zeolite X having a pore size of 8 Angstroms and numerous alkylated amines were produced. Example 3 shows alkylation of diphenylamine with cyclohexene using a rare earth exchanged X zeolite. Again, numerous ring alkylated products were produced and high temperatures, e.g. 300° C. and above apparently being required to weaken the amine-acid bond.

French Pat. No. 1,406,73, which is equivalent to Netherlands Application No. 6,407,636, discloses the preparation of alkylated aromatic compounds having polar substitutionsn thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13X which has undergone a partial exchange with rare earths and having a pore size of 8 Å.

U.S. Pat. No. 3,201,486 discloses prior art processes for alkylating various aromatic hydrocarbons with an olefin using sulfuric acid andn hydrogen fluoride as a catalyst. In the particular reference solid phosphooric acid was used as the catlyst.

U.S. Pat. Nos. 3,178,365; 3,281,483; 4,2559,537; 4,395,372 and 4,393,262 disclose the alkylation of aromatic hydrocarbon compounds with an olefin in the presence of various crystalline alumino-silicates, such as crystalline alumino-silicates having undergone previous transformation by reaction with a nitrogen oxide containing compound, a hydrogen mordenite, a ZSM catalyst exchanged with a Group VIa metal; crystalline alumino-silicates promotd with sulfur dioxide and dealuminated zeolites. The dealuminated, high silica zeolites are preferred as having particular activity for the alkylation of benzene.

Although the prior art has disclosed that a variety of catlytic systems cna be utilized in the alkylation of aromatic hydrocarbons and aromatic amines, teh art also teaches that a variety of reactin products are produced, including both ortho and para-isomers of mononuclear aromatic amines as well as, mono, di and tri alkyl substituted amines. In addition the prior art teaches that neutral to weakly acidic catalysts are preferred for effectign ring alkylation of the aromatic amines. Even though the prior art has suggested preferred catalytic systems such systems also involve batch, liquid phase opeation which may be difficult to operate over an extended period of time, and tend to give more para product. In addition, many of the processes suffer from poor conversion, poor reaction rate and an inability to produce high ortho to para isomer ratios at high conversion.

U.S. Pat. No. 4,224,188 describes the preparation of Al exchanged zeolites for the cracking of petroleum feeds. The catalysts are prepared by ion exchange of $NH_4Y$ or $NaY$ with solutions of $al(N_3)_3$ at $pH=3.2-3.25$. The techniques described in this patent suggest that the preferred method of preparing these materials is to first Al exchange NaY then $NH_4$ exchange the resulting AlNaY zeolite.

K. M. Wang and J. H. Lunsford, J. Catalysis, 24, 62, 1972, report the preparation and catalytic properties of Al exchanged zeolites for the disproportionation of toluene. The zeolites were prepared by contacting NaY zeolite with a solution of 1M $Al(N_3)_3$ for 1–142 hours. The zeolites prepared in this manner where shown to be more active than HY, prepared from $NH_4Y$ for toluene disproportionation. This initial activity was lost however, and the catalyst resulted in the same activity as HY. It was also reported that there was no correlation to the number of Al cations exchange dinto teh zeolite and the catalyst activity.

B. Wichterlova, et all. in the Proceeding of the Fifth International Zeolite Conference also described the Al exchanged zeolites and compared them to dehydroxylated and steamed zeolites for ethylene oligomerization. It was reported that zeolites prepared in this manner were more active for ethylene oligomerization than were HY zeolites prepared by $NH_4$ exchange of Y zeolites.

BRIEF SUMMARY OF THE INVENTION

This present invention is an improved process for alkylating aromatic amines. Aromatic amines are contacted with an olefin or an alcohol in the presence of a zeolite catalyst to form ortho-alkylated products in high selectiveitty relative to N-alkylated products. The space time yields of product formed are increased by carrying out the reaction in the presence of an ion exchanged zeolite in which at least a portion of the exchangeable ion sites have been exchanged with Al cations.

The present process has the ability to effect ring alkylation at high rates and at low temperatures, thus avoiding by-product oligomers and polymers. Additionally, the process may utilize a fixed bed catalytic reactor allowing for continuous vapor or liquid phase operation.

DETAILED DESCRIPTION OF THE INVENTION

The present invention is a process for alkylating aromatic amines generally represented by the formulas:

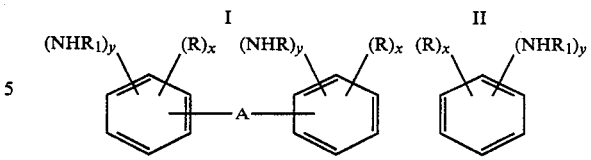

where R is hydrogen, $C_{1-10}$ alkyl or halogen, phenyl, alkoxy, ester, nitrile; $R_1$ is hydrogen or $C_{1-10}$ alkyl; X is 1 or 2, A is $C_{0-4}$ alkylene or NH, y is 1 or 2 except one y in formula I can be zero.

As shown in the above formulas, the aromatic amine can be monoamino or diamino substituted on the aromatic ring. Further, the aromatic amine can be substituted with a variety of substituents which are nonreactive with the olefin nor alcohol in the alkylation reaction. Examples of nonreactive substituents include alkylamino where the alkyl portion has from 1–6 carbon atoms, such as N-ethyl, N-propyl and N-tert-butyl, alkyl where the alkyl substituent has from 1–6 carbon atoms, e.g. ethyl, propyl, tert-butyla nd cyclohexyl, methylcyclohexyl; alkoxy where the carbon content is from 2–6 carbon atoms, and ester, where the carbon ctontent is from 206 carbon atoms.

Many of the amines included within formulas I and II have hydrogen atoms which are reactive in both the ortho and para positions to the amino group. When both of these hydrogens are reactive to alkylatio, one has the ability to selectively produce one isomer in favor of another. In the case of aromatic amines having hydrogen atoms which are reactive in both positions, the para positio nis more thermodynamically stable. In most of the prior art systems, oenn could not simultaneously obtain high conversion of aromatic amine and high selectively to an ortho-alkylated amine. If one went to high conversion of aromatic amine, one obtained higher percentages of the more stable para-isomer. Typically, low conversions, e.g., 20% to 30% were required to achieve a high production of ortho-isomer, e.g., an ortho-para isomer molar ratio of 3 or greater to 1.

Specific examples of aromatic amines suited for alkylation, which include those with active hydrogens in positions ortho and para to the amino group, are aniline, toluidine, xylidene, toluenediamine, xylidenediamine, diphenylamine, methylenedianiline, N-etyl aniline, N-propyl aniline, (N-propylamino)aminotoluene, isobutylaniline, phenyl aniline, phenylenediamine and methylblenzylaniline. Those aromatic amines suited for alkylation having active hdrogen atoms in positions ortho and para to an amino group include aniline and diphenylamine.

Alkylating agents used for practicing the invention are mono aliphatic, acyclic and cyclic olefins adn diolefins such as ethylene, propylene, butene, isobutylene, isoamylene, cyclohexene, 1-methylcyclohexene, 1-methylcyclopentene, butadiene, cyclopentadiene, isoprene and halogenated derivatiges. Typically, these olefins will have from 2 to 8 carbon atoms in teh structure. Additionally in many reactions other materials are commonly used as alkylating agents; e.g., paraffin alcohols such as methanol, ethanol, propanol. In the case where paraffin alcohols are employed, the water from the raction system tends to reduce the ability of the aromatic amine to ring alkylate and when useful alkylation conditions, e.g., temperature, are achieved the product formed contains a hig proportion of the para-isomer.

In the alkylation of aromatic amines, the molar ratio of olefin (or other alkylating agent) to aromatic amine influences the selelctivity of teh reactin. In those cases where the aromatic amine can be alkylated in teh ortho and para positions, the molar ratio of olefin to aromatic amine influences, to some degree, whether the ring alkylation is ortho to the amine or para to the amine. Typically olefin to amine molar ratios will range from about 1 to 20 moles olefin per mole of aromatic amine and preferably 2-8 moles olefin per mole of aromatic amine. The utilization of higher mole ratios of olefin to aromatic amine tends to increase the amount of ortho-alkylated product produced.

It has now been found that high space time yields of alkylated product can be achieved by carrying out the alkylation reaction in the prsence of an ion exchanged zeolite in which at least a portion of the exchangeable ion sites have been exchanged with Al cations. The Al exchanged zeolites have sufficient catalytic activity to effect ring-alkylation of the aromatic amine, and also exhibit greater activity (space time yields) than crystalline molecular sieves which have not undergone Al exchange. The zeolites which can undergo Al exchange and be employed in this reaciton include both synthetic and naturally occurring material. SOme examples of suitable zeolites include: X, Y, L, faujasite, mordenite, offretite, beta, moega, hmelinite, chabazite, clinoptilolite, heulandite, dachiarite, ferrierite, brewsterite, stilbite, epistilbit and the ZSM family. When initially prpared, the cation i nthe crystalline alumino-silicate usually is an alkali metal, typically sodium. At least a portion of the sodium cations are subsequently exchanged with $NH_4$ cations. Subsequently, the ion exchange of Al is exchanged out to achieve between 1-6 Al cations per unit cell, and can be substantially greater depending upon the particular zeolite structure, with one example being, slurrying the zeolite material in distilled water and subsequently adding a volume of between .001-1M and preferably abou 0.1M $Al(N_3)_3$. Other typical sources of solulble Al cations include $Al_2(SO_4)_3$, aluminum acetate and aluminum acetylacetonate. The exchange should be carried ou at a pH between 2-5 and preferably in the 3-4 range. Alternatively, Al alkoxides in non-aqueous media may be used. Prior to exchange with Al cations, it is preferred that the zeolite be predominantly in the $NH_4^+$ form. It is also prferred that the material be heated to about 400° C. if any residual Na ions remain in exchange sites. The zeolites prepared in this way exhibit superior activities to those prepared by simple ion exchange of the zeolite.

Generally, the Al elxchanged zeolites exhibit significant improvements in the space time yields of alkylated products, while still achieving hig selectivity of ortho-alkylated products relative to N-alkylated products. The increase in activity is believed to be the result of an increase in Lewis acid sites in teh zeolite structure, and that Lewis acidity plays a role in determining both the activity and selectivity of the catalysts.

The alkylation of aromatic amines to effect ring alkylation can be carried ou in a fixed bed reactor with the reactants being fed downflow or upflow through the reactor. The reaction can also be carried ou in a stirred autoclave. Temperatures from 50° to 425° C. and pressures of from 50 to 3000 psig are utilized. Although conversion of an aromatic amine to ar ing alkylated product may be greater at temperatures near the upper end of the range specified, the degree of alkylation in the ortho-position as opposed to the para-position may be greatly reduced and olefin polymerization may occur. Higher conversions obtained at high temperatures tend to form higher concentrations of the para-isomer. Thus, to obtain a reaction product with the highest ortho to para-isomer ratio the reaction temperature is controlled to produce a conversion range that will give the highest ortho to para-isomer ratio. For ethylene that temperature will probably be greater than the reaction tempeature for propylene, the propylene temperature will be greater than for iso-butylene. Pressure has some effect on the selectivity to ortho-alkylated product but its effect is much less significant than temperature. Typically prssures used in the operation will range from 500 to 3000 psig for ethylene while prssures of from 50 to 1500 psig will be used for isbutylene.

Reaction time is an important factor in achieving high selectivity to an ortho-alkylated product as opposed to a para-alkylated product. Broadly, the reaction time can be expressed as liqluid hourly space velocity (LHSV) of aromatic amine feed to the ractor and typical values for liquid hourly space velocity are from 0.05 to 6 hours$^{-1}$. If one is operating at relatively high temperatures for the alkylation reaction, the LHSV should be increased somewhat as longer reaction tmes at high temperatures permit increased formation of the para-products. In contrast lower LHSV permit one to obtain high conversion at lower temperatures, low temperatures permitting ring alkylationa t the ortho-position. Thus, by using a combination of an appropriate lower temperature range for a specific olefin and low LHSV one can obtain high conversion at high ortho to para ratios.

While typically ortho-alkylated products are desired, the above reaction condtions can be adjusted to increase the selectivity toward either para-alkylated or N-alkylated products. The Al exchanged zeolite catalysts of the present invention also exhibit improved activity in reactions in which these type of alkylation products are selected for.

The catalyst preparation and examples set out below are presented to further illustrate the invention and are not meant to be limiting.

PREPARATION OF Al EXCHANGED ZEOLITES

Several Al exchanged zeolite samples were prepared under various conditions and procedures as described below.

AlHY (Sample 003.21)

101 g of LZY82 (a commercially available molecular sieve material described as a steam stabilized HY zeolite, Formula=$H_{51}(AlO_2)_{51}(SiO_2)_{141}$ was slurried in 800 cc of distilled $H_2O$. A 0.1M $Al(NO_3)_3$ solution prepared by dissolving 75 g of $Al(NO_3)_3.9H_2O$ in 2 l of $H_2O$ (pH=2.70) was then added to the above slurry. The solution was then refluxed overnight with stirring. The solids were filtered and washed with $H_2O$ until the filtrate was neutral.

AlHY (Sample 003.22)

100 g of LZY62 (NaNH4Y, Formula=$Na_{10}(NH_4)_{46}(AlO_2)_{46}(SiO_2)_{136}$) was treated with 1 l of 0.1M Al($NO_3)_3$ for 2 hours at 75° C. The sample was not heat treated prior to Al exchange (i.e., untreated). The solids were filtered and washed with $H_2O$ until the filtrate was neutral.

AlHY (Samples 003.74, 003.75, 003.76, 003.77)

LZY62, described above, was activated by heating to 400° C. at 2°/min. then holding at 400° C. for 4 hours in a furnace purged with dry $N_2$ followed by humidifying at room temperature and 55% relative humidity. Al exchange was then accomplished by contacting the activated zeolite with 1 l of 0.1M $Al(NO_3)_3$ at different pHs. The pH was adjusted to 2, 3, 4 or 5 by addition of either $RNO_3$ or $NH_4OH$.

|  | SAMPLE NO. |
|---|---|
| pH = 2 | 003.74 |
| pH = 3 | 003.75 |
| pH = 4 | 003.76 |
| pH = 5 | 003.77 |

In addition to the above Al exchanged zeolites, comparative zeolite samples were prepared by the two procedures set out below.

Al₂O₃/HY (Sample 003.17-Comparative)

24.5 g of LLZY82 (described above) was heated overnight at 400° C. 10.92 g of $Al(NO_3)_3.9H_2O$ in a 7.6 cc $H_2O$ was then added to the zeolilte to incipient wetness. The resulting solid was then dried at 100° C. in air and calcined at 300° C. in air overnight.

NH₄Y (Sample 003.31 - Comparative)

LZY62 ws activated to 400° C. in a purged furnace as described above. The zeolite was then exchanged with $NH_4NO_3$ to remove almost all the Na by refluxing in a 1M $NH_4NO_3$ solution.

The formulae and analytical data for the Al exchanged zeolites, as well as for LZY62, LZY82, and the comparative samples are set out in Table 1 below.

TABLE 1

| Catalyst | wt % SiO₂ | wt % Al₂O₃ | Formula |
|---|---|---|---|
| LZY82 | 74.5 | 22.3 | $H_{51}(AlO_2)_{51}(SiO_2)_{141}$ |
| LZY62 | 71.1 | 24.5 | $Na_{10}H_{46}(AlO_2)_{56}(SiO_2)_{136}$ |
| 003.17* | 71.8 | 27.2 | $H_{51}(AlO_2)_{51}(SiO_2)_{142} \cdot 6Al_2O_3$ |
| 003.31* | 75.3 | 24.2 | $H_{51}Na_3(AlO_2)_{54}(SiO_2)_{138}$ |
| 003.21 | 73.4 | 23.5 | $H_{40.6}Al_{35}(AlO_2)_{51}(SiO_2)_{141}$ |
| 003.74 | 72.3 | 25.7 | $H_{46}Na_{4.5}Al_{1.8}(AlO_2)_{56}(SiO_2)_{136}$ |
| 003.75 | 71.9 | 25.3 | $H_{46}Na_6Al_{1.2}(AlO_2)_{56}(SiO_2)_{136}$ |
| 003.76 | 70.8 | 27.2 | $H_{31.5}Na_5Al_{6.5}(AlO_2)_{56}(SiO_2)_{136}$ |
| 003.77 | 68.8 | 28.0 | $H_{20}Na_6Al_{10}(AlO_2)_{56}(SiO_2)_{136}$ |
| 003.22 | 69.3 | 27.7 | $Na_8Al_9H_{21}(AlO_2)_{56}(SiO_2)_{136}$ |

*Comparative

Definition of Terms

For the purpose of the Examples below, the following terms and definitions apply.

Conversion = mole % conversion of aniline
$k_1 = \ln(1 - X) \cdot MHSV$
$X$ = fractional conversion of aniline
MHSV = molar hourly space velocity of aniline = $(LHSV \times 1.02) \div 93.13$
N—Alk = [moles (N—isopropylaniline + N,2 diisopropylaniline)/moles total product] × 100
o-Alk = [moles (2-isopropylaniline + 2,6-diisopropylaniline)/moles total product] × 100
p-Alk = [moles (4-isopropylaniline + 2,4-diisopropylaniline + 2,4,6 triisopropylaniline)/moles total product] × 100

All products were analyzed by capillary gas chromatography.

EXAMPLE 1

Runs were carried ou for alkylatign aniline with propylene at a temperature of 250° C., a pressure between 900–1000 psig, aniline LHSV between 0.250–0.750 and an aniline/propyleine ratio of 1:2 to 1:5. The catalysts employed for the various runs were LZY62; LZY62 with Na removed (sample 003.31); and Al exchanged LY62 zeolite samples 003.22 (unactivated), 003.74, 003.75, 003.76 and 003.77. The results of these runs are set ou in Table 2 below.

TABLE 2

| Catalyst No. | Pre-treatment* T (°C.) | CONV (%) | $k_1 \times 10^3$ ($h^{-1}$) | Selectivities | | |
|---|---|---|---|---|---|---|
| | | | | N—alk | o-alk | p-alk |
| LZY62 | 400 | 28 | 0.9 | 24.0 | 70.1 | 5.85 |
| 003.31 | 400 | 59 | 2.5 | 20.9 | 70.0 | 9.0 |
| 003.22 | | 66 | 3.0 | 24.5 | 65.1 | 10.5 |
| 003.74 | 400 | 70 | 4.6 | 19.0 | 71.2 | 9.1 |
| 003.75 | 400 | 87 | 8.0 | 19.4 | 67.0 | 12.9 |
| 003.76 | 400 | 83 | 6.6 | 18.3 | 70.1 | 11.1 |
| 003.77 | 400 | 47 | 2.4 | 21.6 | 70.0 | 8.4 |

*Heat treatment applied to catalysts prior to exposure to reactants.

As can be seen from the above results, the exchange of Al into LZY62, samples 003.74–003.77, results in considerable improvement in both conversion and activity compared to unexchanged LY62. The data above also show that exchange with $NH_4^+$ to remove $Na^+$ (sample 003.31) improves the activity of LZY62, but is inferior to the Al exchanged samples.

The data reported for the unactivated Al exchanged LY62 (sample 003.22) show an improvement in the activity compared to the unexchanged LZY62 but the improvement is not as great as the Al exchanged samples which were previously activated to 400° C. A comparison of the activated Al exchanged zeolites indicate that a pH range of between 2–5 can be used during the Al exchange, with the best results being at a pH of 3–4.

EXAMPLE 2

Several runs were carried out under the same conditions set out in Example 1 above using different catalysts. The catalysts used for the differentn runs were LZY82, $Al_2O_3$ deposited in the pores of LZY82 (sample 003.17) and Al exchanged LZY82 (sample 003.21). The results of the runs are reported in Table 3 below.

TABLE 3

| Catalyst No. | Activation T (°C.) | CONV (%) | $k_1 \times 10^3$ ($h^{-1}$) | Selectivities | | |
|---|---|---|---|---|---|---|
| | | | | N—alk | o-alk | p-alk |
| LZY82 | 400 | 91 | 6.6 | 18.0 | 68.8 | 12.1 |
| 003.17 | 400 | 89 | 4.9 | 20.1 | 68.5 | 10.1 |
| 003.21 | 400 | 94 | 7.7 | 20.3 | 69.1 | 9.6 |
| 003.21 | 500 | 97 | 9.6 | 18.2 | 70.5 | 10.0 |
| 003.21 | 600 | 82 | 9.4 | 19.6 | 71.0 | 8.9 |
| 003.21 | 750 | 83 | 14.6 | 20.0 | 71.7 | 7.8 |
| 003.21 | 835 | 4 | 0.2 | 19.8 | 77.4 | 2.9 |
| 003.21[1] | 835 | 64 | 2.8 | 12.6 | 74.5 | 8.5 |

[1] Reaction run at 347° C.

The above results show that the exchange of LZY82 with 0.1M $Al(NO_3)_3$ results in an increase in activity compared to unexchanged LZY82 when the catalysts are activated similarly. Additionally, comparing the Al deposited LZY82 zeolite, sample 003.17, with Al excahnged LZY82 (sample 003.21), demonstrates that ion exchange is necessary to realize the increase in catalyst activity.

EXAMPLE 3

Further tests were carried out to verify the role of excahnged Al on the catalytic performance of the zeolites. Several of the Al excahnged LZY62 zeolites described above were washed with 1M NH$_4$NO$_3$ at pH=3 to remove Al from the exchange sites. The sample originally exchanged with Al at pH=3 contained about 1.2 exchanged Al cations per unit cell. Washing with the acid solution resulted in the loss of the exchanged Al as deterined by elemental analysis. The catalyst was then studied for the conversion of aniline and propylene to alkylated products and compared with Al exchanged LZY62. The results are shown in Table 4 below.

TABLE 4

| Catalyst | CONV (%) | k$_1$ (× 1000) | Change |
|---|---|---|---|
| AlY (003.75) | 87 | 8.00 | 0 |
| Extracted (025.18) | 74 | 3.68 | −54% |

The results above indicated that the catalyst with the Al extracted (acid treated) is 54% less active than the originally prepared Al excahnged zeolite. This result is surprising since the literature reports that the treatment of zeolites with acid generally results in a more active catalyst.

Having thus described the present invention, what is now deemed appropriate for Letters Patentn is set out in the following appended claims.

What is claimed is:

1. In a process for alkylating aromatic amines by contacting said amines with an olefin, diolefin or an alcohol tof orm ortho-alkylated products in high selectivity relative to N-alkylated products in the presence of ao zeolite catalyst, the improvement for increasing the space time yields of product formed which comprises: carrying out the alkylation reaction in the presence of an ion exchanged zeolite in which at least a portion of the exchangeable ion sites have been exchanged with Al cations at a pH between 2-5.

2. The process in accordance with claim 1 wherein said aromatic amine is a primary amine.

3. The process in accordance with claim 2 wherein said aromatic primary amine is aniline.

4. The process in accordance with claim 2 wherein teh zeolite is ion exchanged with 0.001-1M solutions of soluble Al cations.

5. The process in accordance with claim 1 wherein the zeolite is ion exchanged with 0.001-1M Al(NO$_3$)$_3$.

6. The process in accordance with claim 1 wherein the zeolite is ion exchanged with 0.1M Al(N$_3$)$_3$.

7. The process in accordance with claim 6 wherein the zeolite is activated to a temperature of at least 400° C. prior to undergoing ion exchange.

8. The process in accordance with claim 1 wherein the space time yield of product formed is increased by at least three fold.

9. The process in accordance with claim 1 wherein the ion exchanged zeolite is selected from the group cosnisting of X, Y, L, faujasite, mordenite, offretite, beta, omega, gmelinite, chabazite, clinoptilolite, heulandite, dachiarite, ferrierite, brewsterite, stilbite, epistilbite and the ZSM family.

10. The process in accordance with claim 1 wherein said alkylation is carried out at a temperature between n50°-425° C. and a pressure between 50-3000 psig.

11. The process in accordance with claim 1 wherein said ion exchanged zeolite contains between 0.1-6 Al cations per unit cell.

12. The process in accordance with claim 1 wherein aniline is alkylated with propylene in teh prsence of an Al exchanged HY zeolite to produce 2-isopropylaniline and 2,6-diisopropylaniline at both high conversion and high selectivity.

13. The process in accordance with claim 1 wherein said reaction is carried ou at an amine LHSV between n0.250-0.750 and with an aminen to olefin ratio between 1:2 to 1:5.

14. The process in accordance with claim 1 wherein the ion exchanged zeolite is heat treated to a temperature of about 400° C. prior to exposure to the reactants.

* * * * *